United States Patent [19]

Bruhl et al.

[11] Patent Number: 4,906,239
[45] Date of Patent: Mar. 6, 1990

[54] HEMORRHOID-TREATMENT ROD

[76] Inventors: Wilhelm Bruhl, Rontorfer Str. 3, 4973 Vlotho-Steinbrundrof; Bernd Gebhardt, Memelstr. 19, 4900 Herford-deutsche Staatsburger, both of Fed. Rep. of Germany

[21] Appl. No.: 704,890

[22] Filed: Feb. 22, 1985

Related U.S. Application Data

[63] Continuation of Ser. No. 492,769, May 9, 1983, abandoned.

[30] Foreign Application Priority Data

May 26, 1982 [DE] Fed. Rep. of Germany ..... 3219727

[51] Int. Cl.$^4$ ............................................. A61M 5/32
[52] U.S. Cl. ..................................... 604/275; 604/104
[58] Field of Search ............... 604/2, 3, 39, 212–216, 604/257, 275, 285, 93, 104

[56] References Cited

U.S. PATENT DOCUMENTS

| 115,285 | 5/1871 | Dithridge | 128/341 |
|---|---|---|---|
| 532,359 | 1/1895 | Bradley | 604/93 |
| 780,710 | 1/1905 | Dickinson | 604/104 |
| 845,249 | 2/1907 | Morris | 604/104 |
| 2,596,597 | 5/1952 | Raymond et al. | 604/279 |
| 2,664,894 | 1/1954 | Gariepy | 604/93 |
| 3,109,427 | 11/1963 | Davidson | 604/275 |
| 3,144,021 | 8/1964 | Diaz | 604/257 |
| 3,225,763 | 12/1965 | Waterman | 604/275 |
| 4,068,663 | 1/1978 | D'Alessandro | 128/232 |

FOREIGN PATENT DOCUMENTS 3318257 12/1983 Fed. Rep. of Germany ...... 604/275

Primary Examiner—C. Fred Rosenbaum
Assistant Examiner—Mario Costantino
Attorney, Agent, or Firm—Sprung Horn Kramer & Woods

[57] ABSTRACT

A hemorrhoid-treatment rod that is shaped like a cone in order to dilate the anus. The outside of the cone may have elevations and depressions. It also has lateral outlets, each of which extends from an interior supply channel to the outside, preferably into one of the depressions. Ointment is forced into the depression and can be massaged into the area to be treating by rotating the rod without being wiped off prematurely.

4 Claims, 1 Drawing Sheet

HEMORRHOID-TREATMENT ROD

This application is a continuation of application Ser. No. 492,769, filed 5/9/83 now abandoned.

BACKGROUND OF THE INVENTION

The present invention relates to a hemorrhoid-treatment rod in the form of a cone-shaped anal dilator.

Hemorroidal complaints normally originate in the anal canal, which contains extremely fine longitudinal slits and pockets that resemble swallows' nests and are open at the top and that are known as the anal sinuses. Since the slits dilate along with the anal sphincter during defecation, feces can get established inside them. Feces can also penetrate into the sinuses during passage.

Although hemorrhoidal ointments exist that are in themselves effective, really successful treatment can be expected only when the ointment can be applied into the slits and, if necessary, into the anal sinuses as well.

Anal-treatment dilators in the form of a hollow, relatively thin-walled, rotationally symmetrical cone are known. The cone is dimensioned to dilate the anus and hence the slits as well. Getting the ointment into the slits and sinuses, however, is often impeded because most of the ointment, which is preliminarily applied to the surface of the cone, gets wiped off while the instrument is being introduced into the outer region of the anus.

Screwing a slender tube onto the threaded connector of the ointment container is also known. Such a tube can also be slightly cone-shaped. A tube with an outlet is also known, however successful treatment is impeded in this case from the very fact that the tubes are much too small to satisfactorily dilate the anus. Thus, the ointment does not penetrate deeply enough, and often not at all, into the slits, which are as slender as hairs, or into the sinuses.

SUMMARY OF THE INVENTION

The present invention is accordingly intended as a generic hemorrhoid-treatment tube that will ensure deep enough penetration of the ointment into the slits and sinuses.

With a hemorrhoid-treatment tube in the form of a cone-shaped anal dilator as a point of departure, the invention achieves its objective in that the cone has lateral outlets each of which leads from a supply channel to the outside surface of the dilator.

In contrast to conventional anal dilators, the ointment can now be introduced into the region to be treated once the anus, and hence the slits, have been dilated. The ointment emerges from each lateral outlet on the outside surface of the cone. With no risk of the ointment becoming prematurely wiped off, there will be plenty of ointment in the dilated anal canal. In a preferred embodiment, in which the outer surface has elevations and depressions, which each outlet leading into a depression the ointment can be introduced with a rotating motion, which will also generate a massaging action on the part of the elevations and depressions, deep into the dilated slits. Moving the cone in and out several times will make it possible to fill the sinuses as well with ointment, a result that will be augmented in accordance with a preferred embodiment of the invention in that the tip of the outside of the cone is surrounded by a rounded torus that promotes penetration of the ointment into the pocket-shaped sinuses when the cone is extracted. In another preferred embodiment of the hemorrhoid-treatment rod corrugations with crests and depressions are distributed uniformly around its surface and extending longitudinally over it. Preferably, the lateral outlets are two longitudinal and diametrically opposed outlet slots. In a further preferred embodiment the torus is situated between the round tip of the cone and the outlets. Still further, the base of the cone has a cylindrical section provided with a threaded connection for a container.

One example of an embodiment of such a rod will now be specified with reference to the drawing, in which

DETAILED DESCRIPTION OF THE INVENTION

Figure 1:
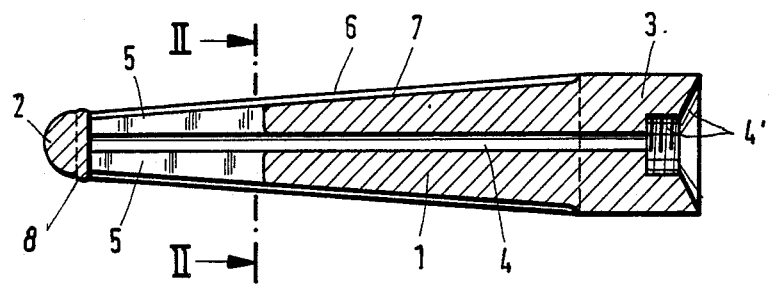
FIG. 1 is a longitudinal section through a hemorrhoid-treatment rod in accordance with the invention.
Figure 2:
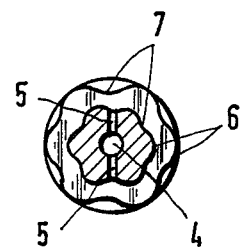
FIG. 2 is a section through the line II—II in FIG. 1.

Referring now to FIGS. 1 and 2, the illustrated hemorrhoid-treatment rod is basically cone-shaped. The cone 1 that forms the main body has a rounded tip 2 and a cylindrical section 3 at the base. Cylindrical section 3 is provided with a threaded connection 4' for the threaded connector of a container of ointment and is shaped so that the treatment rod can in itself be screwed onto the container.

A supply channel 4 runs through the middle of cone 1 and cylindrical section 3 and extends into the vicinity of tip 2, where lateral outlets 5 branch off from it. The outlets 5 in the illustrated embodiment are two longitudinal and diametrically opposed outlet slots.

The outside of cone 1 is provided with elevations and depressions. The elevations and depressions in the illustrated embodiment are corrugations with crests 6 and depressions 7 distributed uniformly around its surface and extending longitudinally from cylindrical section 3 to the vicinity of tip 2. Each outlet slot 5 is situated in one of these depressions 7.

In the vicinity of the tip 2, between rounded tip 2 and the ends of lateral outlets 5 is a continuous rounded torus that extends slightly above the outside surface and beyond the crests 6 of the corrugations as well. This torus promotes penetration of the ointment into the pocket-shaped anal sinuses when the treatment rod is extracted.

The treatment rod is screwed onto an ointment container (not shown) and introduced into the anus. Cone 1 is shaped in such a way as to function as an anal dilator. The diameter of the base of the cone is configured to be appropriate for this purpose and it has found out to be practical for the cone to be about 8–10 cm long and to taper at an angle of about 10°.

Subsequent to dilation of the anus, which will also entail dilation of the extremely fine slits, ointment can be forced through the supply channel 4 in the screwed-on tube, out of lateral outlets 5, and into the anal canal. The treatment tube is rotated back and forth to massage the ointment deeply into the dilated slits, promoted by the corrugations on the surface of cone 1. The pocket-shaped sinuses can also be filled with ointment by moving the rod in and out several times, an effect that is augmented by torus 8.

It will be appreciated that the instant specification and claims are set forth by way of illustration and not limitation, and that various modifications and changes may be made without departing from the spirit and scope of the present invention.

What is claimed is:

1. A hemmorrhoid-treatment tube comprising: a cone-shaped anal dilator having an internal supply channel receptive of ointment, an outside surface having alternating longitudinally extending elevations and depressions comprising corrugations with crests and depressions distributed uniformly around the outside surface of the dilator and extending longitudinally thereover along substantially the entire length of the dilator, axially elongated outlet slots each extending rearwardly from the smaller end of the dilator and each extending radially between the supply channel and one longitudinally extending surface depression along the entire length of the slot, whereby ointment supplied from the supply channel is communicated via the slots to the depressions along a considerably length thereof and applied by the dilating and massaging action resulting from the rotation of the dilator, a rounded tip at the smaller end of the dilator and a continuous rounded torus projecting from the outside surface of the dilator in the vicinity of the tip.

2. The hemorrhoid-treatment tube according to claim 1, wherein the outlet slots comprise two longitudinal and diametrically opposed outlet slots.

3. The hemmorrhoid-treatment tube according to claim 1, wherein the torus is disposed between the rounded tip of the cone and the end of the outlet slots.

4. The hermorrhoid-treatment tube according to claim 1, further comprising a cylindrical section connected to the larger end of the cone and having a threaded connection to the supply channel for a supply of ointment.

* * * * *